United States Patent
Fazioni et al.

(10) Patent No.: US 8,318,503 B2
(45) Date of Patent: Nov. 27, 2012

(54) METHOD FOR DETERMINING THE AMOUNT OF CONJUGATED TAXANE IN POLYGLUT ACID-TAXANE CONJUGATES

(75) Inventors: Stefano Fazioni, Meda (IT); Keith Hovda, Kent, WA (US); Valeria Livi, Sesto San Giovanni (IT); Marc McKennon, Seattle, WA (US); Luigi Siviero, Vimercate (IT); Holly Spoonemore, Bellevue, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 222 days.

(21) Appl. No.: 12/529,762

(22) PCT Filed: Mar. 5, 2008

(86) PCT No.: PCT/EP2008/001746
§ 371 (c)(1),
(2), (4) Date: Feb. 17, 2010

(87) PCT Pub. No.: WO2008/107174
PCT Pub. Date: Sep. 12, 2008

(65) Prior Publication Data
US 2010/0151582 A1 Jun. 17, 2010

(30) Foreign Application Priority Data

Mar. 6, 2007 (EP) .................................... 07004574

(51) Int. Cl.
*G01N 33/15* (2006.01)

(52) U.S. Cl. ............................................ 436/93; 436/91
(58) Field of Classification Search .................... 436/85, 436/86, 91, 92, 93, 96
See application file for complete search history.

(56) References Cited

U.S. PATENT DOCUMENTS
6,281,368 B1 8/2001 McChesney et al.

FOREIGN PATENT DOCUMENTS
WO 97/33552 A1 9/1997
WO 03/004482 A1 1/2003

OTHER PUBLICATIONS

Lan, Ruoxi et al. "Design and Synthesis of the CB1 selective cannabinoid antagonist AM281: A potential human SPECT ligand." AAPS Pharmsci (1999) 1 4.*
International Search Report and Written Opinion PCT/EP2008/001746, dated May 28, 2008.
Shaffer, Scott A. et., al,Cancer Chemotherapy Ano Pharmacology, 59(4); 537-548 (2006), XP002437705.

* cited by examiner

*Primary Examiner* — Yelena G Gakh
*Assistant Examiner* — Christopher A Hixson
(74) *Attorney, Agent, or Firm* — Seed IP Law Group PLLC

(57) ABSTRACT

The invention relates to a method for determining the amount of conjugated taxane, in particular paclitaxel, in a PGA-taxane conjugate said method comprising: a) reacting the PGA-taxane conjugate with a compound formula (I): $R^1R^2N-NH_2$ (I), wherein $R^1$ and $R^2$ are as defined in the description; to give a unbound taxane and a PGA hydrazide and b) determining the amount of unbound taxane.

9 Claims, No Drawings

METHOD FOR DETERMINING THE AMOUNT OF CONJUGATED TAXANE IN POLYGLUT ACID-TAXANE CONJUGATES

CROSS-REFERENCE TO RELATED APPLICATIONS

The present application is a national phase entry under 35 U.S.C. §371 of International Application No. PCT/EP2008/001746, filed Mar. 5, 2008, published in English, which claims the benefit of European Patent Application No. 07 004 574.5, filed Mar. 6, 2007. The disclosures of said applications are incorporated by reference herein.

BACKGROUND OF THE INVENTION

Paclitaxel (available on the market as Taxol® Injection) is the prototype of chemotherapeutic taxanes, which binds to β-tubulin, promotes the assembly of this protein into microtubules and stabilizes them, eventually causing cell death. Paclitaxel poliglumex (PPX, chemical name N-(L-pyroglutamyl)-[poly(L-glutamyl)]-L-glutamic acid partially γ-esterified with (2'R,3'S)-3'-benzoylamido-1'-[[4,10β-bis(acetoxy)-2α-(benzoyloxy)-1,7β-dihydroxy-9-oxo-5,20-epoxytax-11-en-13α-yl]oxy]-1'-oxo-3'-phenylpropan-2'-ol), hereinafter referred to as PPX, is the ester conjugate of α-poly-L-glutamic acid (PGA) and paclitaxel wherein the latter is covalently bound to PGA through the 2'-hydroxy position.

PPX is currently under study for use in non-small cell lung cancer (NSCLC) and ovarian cancer. Paclitaxel is released after uptake and proteolytic/hydrolytic degradation of the conjugate in a tumor tissue.

The molecular formula and molecular weight of PPX are distributions because the polymerization degree of α-poly-L-glutamic acid and the number of conjugation sites with paclitaxel vary according to the manufacturing process. The average molecular mass of PPX is approximately 40,000 Daltons, determined by non-aqueous gel permeation chromatography with detection by multi angle laser light scattering. Approximately 35% by weight paclitaxel is present in the bound form in the conjugate, which amounts to about one paclitaxel ester linkage per 11 monomer units. Methods for the synthesis of PPX are disclosed in PCT publication WO97/33552.

Among manufacturing tests to be performed on PPX, both as active ingredient and as finished pharmaceutical product, assays for the quantification of conjugated paclitaxel and related taxane-based impurities are prescribed. However, the latter assay cannot be carried out on PPX as such and deesterification is required to liberate paclitaxel. Tetrahedron Letters, (1995), 36(12), 2001-2004 discloses a procedure for the hydrolytic cleavage of various esters of paclitaxel using basic hydrogen peroxide/tetrahydrofuran mixtures, wherein the 2'-acetate of peracetylated paclitaxel is hydrolyzed faster than the 10-acetyl position. When this method is applied to paclitaxel, the reported product is 10-deacetylpaclitaxel (10-DAT). A known procedure initially employed for the quantification of conjugated paclitaxel and related taxane impurities in PPX comprises exhaustive aqueous hydrolysis of PPX with sodium bicarbonate/peroxide with concomitant extraction of paclitaxel and related taxane impurities in $CHCl_3$ and quantification by HPLC. The addition of $CHCl_3$ as a second phase allows for extraction of the liberated taxanes immediately after hydrolysis, preventing most of the 10-DAT formation. The hydrolysis reaction, however, causes significant degradation of paclitaxel, principally to 10-deacetylpaclitaxel (10-DAT) and 20% levels of 10-DAT were common using this method, as the biphasic system did not completely suppress hydrolysis at the 10 position. As a result, the peaks of both paclitaxel and 10-DAT are quantified together and reported as paclitaxel+10-DAT. To be able to correct the amount of paclitaxel+10-DAT obtained from the hydrolysis method to total paclitaxel only, a second method using NMR quantification needs to be performed to quantify the amount of indigenous conjugated 10-DAT. Thus, the formation of degradation products and the change of the conjugated taxane profile is a clear drawback of this procedure. Moreover, the chromatographic conditions are not specific for the degradation compound.

There is therefore the need for an improved method for the quantification of PGA-conjugated paclitaxel and other PGA-conjugated taxanes.

DETAILED DESCRIPTION OF THE INVENTION

Accordingly, the present invention relates to a method for determining the amount of conjugated taxane in PGA-taxane conjugates which comprises the hydrolysis of the conjugate in a non-aqueous medium, using a hydrazine-derivative in place of the hydroperoxy anion.

In greater detail, the method of the invention comprises the reaction of a PGA-taxane conjugate with a compound formula (I):

$$R^1R^2N-NH_2 \qquad (I)$$

wherein
$R^1$ and $R^2$ are independently selected from $C_1$-$C_{10}$-alkyl, $C_1$-$C_{10}$ hydroxyalkyl, $C_3$-$C_{10}$ alkenyl, $C_3$-$C_{10}$-hydroxyalkenyl, $C_3$-$C_{10}$-alkynyl, $C_3$-$C_{10}$-hydroxyalkynyl, aryl, heteroaryl; or $R^1$ and $R^2$ taken together with the nitrogen atom to which they are linked form a 3-8 membered heterocyclic ring optionally containing up to three heteroatoms selected form O, S and N and optionally substituted with up to two hydroxy groups;
to give unbound taxanes and a PGA-hydrazide
followed by determination of the unbound taxane.

For the purposes of the present invention, a PGA-taxane conjugate is an α-poly-L-glutamic acid (PGA) wherein one or more γ-carboxy groups of the glutamic acid repeating unit are esterified with a taxane molecule through the 2'-hydroxy group of the latter. Typically, PGA contains from 60 to 310 monomer units and has a molecular mass ranging from 8,000 to 40,000 Dalton. A PGA-hydrazide is a hydrazide resulting from the reaction of the ester groups linking the 2'-hydroxy groups of the taxane to the γ-carboxy groups of the glutamic acid repeating units of PGA in the PGA-taxane conjugate with the hydrazine of formula (I). In the PGA-hydrazide, the nitrogen of the primary amino group of the compound of formula (I) is bound to the carbonyl of the γ-carboxy group of the glutamic acid repeating unit of PGA.

As used herein, taxane means paclitaxel, docetaxel, or other taxanes that may be either isolated from natural sources such as the Yew tree, or from cell culture, or chemically synthesized, such as 10-deacetylpaclitaxel, 7-epipaclitaxel, cephalomannine, 7-epi-cephalomannine, and N-debenzoyl-N-phenylacetylpaclitaxel. The most preferred taxane is paclitaxel.

As used herein, the term "$C_1$-$C_{10}$-alkyl" refers to a straight or branched saturated hydrocarbon group containing from 1 to about 10 carbon atoms, such as methyl, ethyl, propyl (e.g., n-propyl and isopropyl), butyl (e.g., n-butyl, isobutyl, s-butyl, t-butyl), pentyl (e.g., n-pentyl, isopentyl, neopentyl) and the like.

As used herein, the term "$C_1$-$C_{10}$-hydroxyalkyl" refers to a $C_1$-$C_{10}$-alkyl group which can be substituted by up to three hydroxyl groups.

As used herein, the term "$C_3$-$C_{10}$-alkenyl" refers to an alkyl group which contains from 3 to about 10 carbon atoms and having one or more double carbon-carbon bonds.

Examples of alkenyl groups include ethenyl, propenyl, butenyl, pentenyl, hexenyl, butadienyl, pentadienyl, hexadienyl, and the like.

As used herein, the term "$C_3$-$C_{10}$-hydroxyalkenyl", refers to a $C_3$-$C_{10}$-alkenyl group which can be substituted with up to three hydroxyl groups on the carbon atoms not engaged in carbon-carbon double bonds.

As used herein, "$C_3$-$C_{10}$-alkynyl" refers to an alkyl group containing from 3 to about 10 carbon atoms and having one or more triple carbon-carbon bonds. Examples of alkynyl groups include ethynyl, propynyl, butynyl, pentynyl, and the like.

As used herein, the term "$C_3$-$C_{10}$-hydroxyalkynyl" refers to a $C_3$-$C_{10}$-alkynyl group which can be substituted with up to three hydroxyl groups on the carbon atoms not engaged in carbon-carbon triple bonds.

As used herein, the term "$C_1$-$C_3$-alkyl" refers to a straight or branched saturated hydrocarbon group containing from 1 to 3 carbon atoms.

As used herein, the term "$C_1$-$C_3$-halogenoalkyl" refers to a $C_1$-$C_3$-alkyl group substituted with up to three halogen (i.e. F, Cl, Br, I) atoms.

As used herein, the term "$C_1$-$C_3$-alkoxy" refers to O—$C_1$-$C_3$-alkyl groups such as methoxy, ethoxy, n-propoxy and isopropoxy.

As used herein, the term "$C_1$-$C_3$-thioalkoxy" refers to S—$C_1$-$C_3$-alkyl groups, i.e. methylthio, ethylthio, n-propylthio and isopropilthio.

As used herein, "aryl" refers to aromatic carbocyclyl groups including monocyclic or polycyclic aromatic hydrocarbons such as phenyl, naphthyl, anthracenyl, phenanthrenyl, indanyl, indenyl, and the like, which may be optionally substituted with halogen, $C_1$-$C_3$-alkyl, $C_1$-$C_3$-halogenoalkyl, $C_1$-$C_3$-alkoxy, $C_1$-$C_3$-thioalkoxy, or nitro groups.

As used herein, "heteroaryl" groups are aromatic heterocarbocyclyl groups and include monocyclic and polycyclic aromatic hydrocarbons containing at least one heteroatom ring member such as sulfur, oxygen, or nitrogen and which may be optionally substituted with halogen, $C_1$-$C_3$ alkyl, $C_1$-$C_3$-halogenoalkyl, $C_1$-$C_3$-alkoxy, $C_1$-$C_3$-thioalkoxy, or nitro groups. Heteroaryl groups include pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, and the like.

Examples of compounds of formula (I) that can advantageously be used to carry out the invention include N,N-dimethylhydrazine, phenylhydrazine, 4-bromophenylhydrazine, 4-isopropylphenylhydrazine, 4-methoxyphenylhydrazine, 1-methyl-1-phenylhydrazine, 1-aminopyrrolidine, 1-amino-2,6-dimethylpiperidine, 1-amino-cis-2,6-dimethylpiperidine, (S)-(−)-1-amino-2-(methoxymethyl)pyrrolidine, (R)-(+)-1-amino-2-(methoxymethyl)pyrrolidine, 4-aminomorpholine, 1-aminopiperidine, 1-amino-4-methylpiperazine, 1-amino-4-(2-hydroxyethyl)piperazine, 1-amino-homopiperidine. Preferred reagents are N,N-dimethylhydrazine, phenylhydrazine, 4-aminomorpholine and 1-aminopiperidine, the most preferred being 4-aminomorpholine.

The reaction between the PGA-taxane conjugate and (I) is carried out in an aprotic organic solvent such as dimethylformamide, dimethylsulfoxide, N-methylpyrrolidinone and the like. According to a preferred embodiment of the invention, a sample of PPX or of a PPX-containing medicament is dissolved or suspended in dimethylformamide or dimethylsulfoxide to provide a concentration of PPX between 25 and 52 mg/ml, then 4-aminomorpholine or a solution of 4-aminomorpholine in trifluoroacetic acid is added. The ratio between the PPX solution and 4-aminomorpholine/trifluoroacetic acid is between 1:0.3 v/v and 1:0.5 v/v. The mixture is stirred at a temperature between about 20° C. and about 42° C. for a time ranging from about 2 hours to about 24 hours.

The determination of the unbound taxane can be carried out by HPLC or by any other methods known in the art for the quantitative analysis of taxanes.

According to a preferred embodiment of the invention, a PPX sample or of a PPX-containing medicament is dissolved in dimethylsulfoxide to provide a concentration of PPX between 48 and 52 ng/ml and a solution of 4-aminomorpholine in trifluoroacetic acid is added wherein the ratio of trifluoroacetic acid to 4-aminomorpholine is 0.017:1 v/v. The ratio of PPX solution to 4-aminomorpholine/trifluoroacetic acid is 1:0.5 v/v. The mixture is stirred and temperature and reaction time are monitored until approximately 2%-7% of the conjugated taxane is released. Preferably, the temperature is maintained in the range of about 38-42° C. and the reaction time ranges from about 1.9 to about 2.1 hours. Within these ranges the purity profile does not change as a function of conversion. After addition of acetonitrile the solution is ultrafiltered by centrifugation to remove the unreacted polymer and then directly injected into a HPLC column to determine the percent area of paclitaxel and of each taxanes impurity. UV response factors reported in the USP or calculated are applied to transform the % area of known impurities in w/w % relative to paclitaxel; the amount of other unknown impurities is instead calculated as % area. Paclitaxel's purity is calculated by subtracting the sum of all impurities from 100%.

The mild reaction conditions of the method of the invention reduce the amount of paclitaxel degradation from about 20% to less than 0.5% and allow for the quantification of 10-DAT above 0.2%, thereby eliminating the need for NMR quantification.

The invention will be now illustrated in greater detail by means of the following examples.

EXAMPLES

To demonstrate the accuracy and sensitivity of the method of the invention, paclitaxel was spiked with a known amount (10% w/w) of three chemically different taxanes and then conjugated to α-poly-(L)-glutamic acid in amount of 37% w/w. Two of the three taxanes were synthetic impurities (cephalomannine and 7-epi-cephalomannine), the third was a degradation impurity (7-epipaclitaxel). Three different spiking levels (1.2%, 9.8%, 28% w/w) were investigated for each taxane in the range within the quantitation limit and the upper specification limit. All three impurities were recovered in amount between 100% and 115%, which was deemed to be acceptable for the intended use of the method. A representative example of this experiment is given in Example 1. The routine release analysis of a PPX batch is reported in Example 2.

Example 1

A solution of paclitaxel/7-epipaclitaxel conjugate was prepared by accurately weighting 350±5 mg of the conjugate in a 10 mL flask and dissolving with dimethylsulfoxide. The solution was diluted to volume with the same solvent. 250±2.5 mg of PPX (Pharmaceutical Grade) were accurately weighed in a 5 mL flask. 0.085 mL of the spiking solution (corresponding to a spiking level of 1.2% w/w) was added in the same flask and diluted to volume with dimethylsulfoxide. The aminolysis reaction was then performed according to the general procedure given in Example 2 and analysed by HPLC. Recovery of 7-epipaclitaxel was 110.7%.

Example 2

250 mg of PPX (Active Pharmaceutical Ingredient), accurately weighed, were transferred into a 5 mL flask. After dissolution with dimethylsulfoxide the sample was diluted to volume with the same solvent. 1.0 mL of this solution was transferred into a 5 mL conical bottom vial. A triangular magnetic stirring bar was placed in each vial and 0.5 mL of a solution comprised of trifluoroacetic acid and 4-aminomorpholine in a ratio of 0.017:1 (0.034 mL of TFA added to 2.0 mL of 4-aminomorpholine) were added. The vial was tightly capped, placed on a thermostated stirring water bath at 40° C.±2° C. and stirred for 2±0.1 hours. At the end of the reaction the vial was allowed to cool slowly to room temperature over about 10 minutes before addition of 0.75 mL of acetonitrile. After mixing, the sample was transferred to centrifuge filters (molecular mass cut-off=10,000 daltons) and centrifuged for 1 hour at 3000×g. 1 mL of the sample was transferred to an HPLC vial, added with 10 μL of glacial acetic acid and analyzed by HPLC for the determination of the taxane content using a Zorbax 300SB-C8 column, 4.6×100 mm 3.5 μm, Agilent Cat. No. 861973-906, maintained at 40° C. and eluting with a water/acetonitrile gradient mixture from 20% acetonitrile/80% water to 90% acetonitrile 10% water in 60 minutes, with UV detection at 227 nm.

The results (average of six replicates and expressed as area % corrected for the Relative Response Factor) are reported in Table 1.

TABLE 1

| Taxane | Area % corrected for RRF |
| --- | --- |
| Baccatin III: | Below Reporting Level |
| 10-DAT: | 0.24% |
| Cephalomannine: | 0.22% |
| OR1: | Below Reporting Level |
| OR2 + OR3 | 0.39% |
| 7-epi-10-Deacetylpaclitaxel: | Below Reporting Level |
| Paclitaxel: | 98.80% |
| 7-epi-Paclitaxel: | 0.16% |
| Unknown (RRT 1.13): | Below Reporting Level |
| Unknown (RRT 1.28): | Below Reporting Level |

Impurities indicated as $OR_1$, $OR_2$ and $OR_3$ are conjugates between α-poly-(L)-glutamic acid and taxanes having the following formula:

Formula

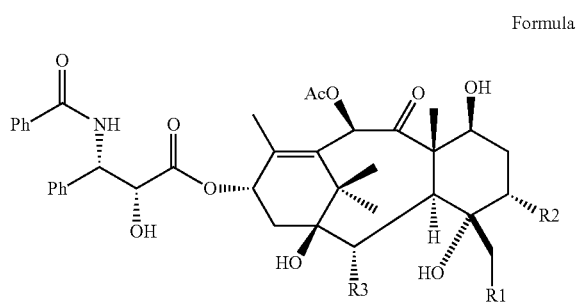

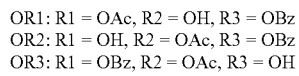

OR1: R1 = OAc, R2 = OH, R3 = OBz
OR2: R1 = OH, R2 = OAc, R3 = OBz
OR3: R1 = OBz, R2 = OAc, R3 = OH

The invention claimed is:

1. A method for determining the amount of conjugated taxane in a polyglutamic acid-taxane conjugate wherein one or more taxane molecules are linked through the 2'-hydroxy position to the γ-carboxy group of α-poly-L-glutamic acid said method comprising the steps of:

a) reacting the polyglutamic acid-taxane conjugate with a compound of formula (I):

$$R^1R^2N-NH_2 \qquad (I)$$

wherein $R^1$ and $R^2$ are independently $C_1$-$C_{10}$-alkyl, $C_1$-$C_{10}$-hydroxyalkyl, $C_3$-$C_{10}$-alkenyl, $C_3$-$C_{10}$-hydroxyalkyl, $C_3$-$C_{10}$-alkynyl, $C_3$-$C_{10}$-hydroxyalkynyl, aryl, heteroaryl; or $R^1$ and $R^2$ taken together with the nitrogen atom to which they are linked form a 3-8 membered heterocyclic ring optionally containing up to three heteroatoms selected from O, S and N and optionally substituted with up to two hydroxy groups;

to give an unbound taxane and a polyglutamic acid hydrazide; and (b) determining the amount of unbound taxane.

2. The method according to claim 1 wherein the amount of unbound taxane is determined by HPLC.

3. The method according to claim 1 wherein the taxane conjugated to polyglutamic acid is selected from paclitaxel, docetaxel, 10-deacetylpaclitaxel, 7-epipaclitaxel, cephalomannine, 7-epicephalomannine, and N-debenzoyl-N-phenylacetylpaclitaxel.

4. The method according to claim 1 wherein the taxane conjugated to polyglutamic acid is paclitaxel.

5. The method according to claim 1 wherein the compound of formula (I) is selected from N,N-dimethylhydrazine, phenylhydrazine, 4-bromophenylhydrazine, 4-isopropylphenylhydrazine, 4-methoxyphenylhydrazine, 1-methyl-1-phenylhydrazine, 1-aminopyrrolidine, 1-amino-2,6-dimethylpiperidine, 1-amino-cis-2,6-dimethylpiperidine, (S)-(−)-1-amino-2-(methoxymethyl)pyrrolidine, (R)-(+)-1-amino-2-(methoxymethyl)pyrrolidine, 4-aminomorpholine, 1-aminopiperidine, 1-amino-4-methylpiperazine, 1-amino-4-(2-hydroxyethyl)piperazine and 1-amino-homopiperidine.

6. The method according to claim 1 wherein the compound of formula (I) is selected from N,N-dimethylhydrazine, phenylhydrazine, 4-aminomorpholine and 1-aminopiperidine.

7. The method according to claim 1 wherein the compound of formula (I) is a 4-aminomorpholine.

8. The method according to claim 7 wherein step a) is carried out in dimethylformamide or dimethylsulfoxide at a temperature ranging from 20 to 42° C.

9. The method according to claim 8 wherein claim a) is carried out in dimethylsulfoxide at a temperature between 38 and 42° C.

* * * * *